US012569647B2

(12) United States Patent
Duan et al.

(10) Patent No.: US 12,569,647 B2
(45) Date of Patent: Mar. 10, 2026

(54) CATHETER SUPPORT APPARATUS AND TRANSLUMINAL INTERVENTION SYSTEM

(71) Applicants:CTC Medical Technology (Beijing) Co., LTD., Beijing (CN); QINGDA CTC (XIAMEN) Medical Technology Co., Ltd., Xiamen (CN)

(72) Inventors: Hailong Duan, Beijing (CN); Meng Shao, Beijing (CN); Lei Zhao, Beijing (CN); Huagen Liu, Beiing (CN); Xiaoming Li, Beijing (CN)

(73) Assignees: CTC Medical Technology (Beijing) Co., LT, Beijing (CN); QINGDA CTC (XIAMEN) Medical Technology Co., Ltd., Xiamen (CN)

( * ) Notice: Subject to any disclaimer, the term of this patent is extended or adjusted under 35 U.S.C. 154(b) by 0 days.

(21) Appl. No.: 19/100,785

(22) PCT Filed: Aug. 14, 2023

(86) PCT No.: PCT/CN2023/111220
§ 371 (c)(1),
(2) Date: Feb. 3, 2025

(87) PCT Pub. No.: WO2024/037357
PCT Pub. Date: Feb. 22, 2024

(65) Prior Publication Data
US 2025/0256061 A1 Aug. 14, 2025

(30) Foreign Application Priority Data
Aug. 16, 2022 (CN) .......................... 202210983237.0

(51) Int. Cl.
*A61M 25/00* (2006.01)
*A61M 25/02* (2006.01)

(52) U.S. Cl.
CPC .......... *A61M 25/005* (2013.01); *A61M 25/02* (2013.01); *A61M 2025/0059* (2013.01); *A61M 2025/028* (2013.01)

(58) Field of Classification Search
CPC ................ A61M 25/005; A61M 25/02; A61M 2025/0059; A61M 2025/028; A61M 25/01; A61M 25/10
See application file for complete search history.

(56) References Cited

U.S. PATENT DOCUMENTS

| | | | |
|---|---|---|---|
| 3,330,105 A | 7/1967 | Weber | |
| 3,503,579 A | 3/1970 | Sam | |
(Continued)

FOREIGN PATENT DOCUMENTS

| | | |
|---|---|---|
| CN | 1203651 A | 12/1998 |
| CN | 1401152 A | 3/2003 |
(Continued)

OTHER PUBLICATIONS

Nov. 9, 2023—(PCT/CN) Search Report—App 2023-111220—with translation.
(Continued)

*Primary Examiner* — James D Ponton
*Assistant Examiner* — John A Doubrava
(74) *Attorney, Agent, or Firm* — Banner & Witcoff, Ltd.

(57) ABSTRACT

Disclosed are a catheter support apparatus and a transluminal intervention system. The catheter support apparatus comprises a plurality of flexible supporting strips. A plurality of meshing units arranged at intervals in a strip length direction are formed on the flexible supporting strips. The meshing units of the plurality of flexible supporting strips are at least partially meshed to jointly surround, define, and form a catheter placing cavity for accommodating a catheter. The flexible supporting strips are adopted such that, by
(Continued)

means of the meshing units on the flexible supporting strips, the plurality of flexible supporting strips can be meshed and formed into the catheter placing cavity. By means of the catheter placing cavity, the catheter can be accommodated to enable wrapping of the catheter, thereby ensuring the support for the catheter. The catheter support apparatus has an effect of a certain anti-bending torque, and it has a simple structure and is easy to operate, thereby ensuring the smooth completion of an interventional surgery.

20 Claims, 12 Drawing Sheets

(56)                    References Cited

U.S. PATENT DOCUMENTS

| | | | |
|---|---|---|---|
| 5,108,350 A | | 4/1992 | Szpakowski |
| 5,364,368 A | * | 11/1994 | Kauffman ............. A61M 25/02 |
| | | | 128/DIG. 6 |
| 6,107,565 A | | 8/2000 | O'Rourke |
| 7,234,292 B1 | | 6/2007 | O'Rourke et al. |

| | | |
|---|---|---|
| 2003/0199831 A1 | 10/2003 | Morris et al. |
| 2017/0258489 A1 | 9/2017 | Galili et al. |
| 2018/0008407 A1 | 1/2018 | Maimon et al. |
| 2019/0223977 A1 | 7/2019 | Galili et al. |
| 2019/0290372 A1 | 9/2019 | Arnold et al. |
| 2020/0179657 A1 | 6/2020 | Liu |
| 2022/0233814 A1 | 7/2022 | Mullins et al. |

FOREIGN PATENT DOCUMENTS

| | | |
|---|---|---|
| CN | 111601983 A | 8/2020 |
| CN | 115040756 B | 11/2022 |
| CN | 115054342 B | 12/2022 |
| DE | 3139735 A1 | 4/1983 |
| EP | 1475123 A1 | 11/2004 |
| GB | 1216093 A | 12/1970 |

OTHER PUBLICATIONS

Sep. 30, 2022—(CN) Notice of Allowance—App 202210983237. 0—with translation.
Sep. 16, 2025—(EP) Search Report—Appln. 23854261.7.

* cited by examiner

CATHETER SUPPORT APPARATUS AND TRANSLUMINAL INTERVENTION SYSTEM

CROSS-REFERENCE TO RELATED APPLICATIONS

The present application is a U.S. National Phase filing of International Application No. PCT/CN2023/111220, filed on Aug. 4, 2023, and claiming the priority of Chinese Patent Application No. 202210983237.0, entitled "Catheter Support Apparatus and Transluminal Intervention System" and filed with China National Intellectual Property Administration on Aug. 16, 2022, the content of which is incorporated herein by reference in its entirety.

FIELD OF THE INVENTION

The present disclosure relates to the technical field of interventional treatment, and in particular, to a catheter support apparatus and a transluminal intervention system.

BACKGROUND OF THE INVENTION

In the interventional treatment, a catheter or an instrument "intervenes" in almost all vascular branches, digestive tracts and other specific parts in the human body for treatment of a disease. For a neoplastic disease, endovascular intervention refers to inserting a catheter into a blood vessel that supplies a tumor and injecting chemotherapy drugs through catheter the so as to enable precise targeted treatment by chemotherapy drugs, or refers to blocking the blood vessel (embolization) and thus cutting off blood supply of tumour cells so as to cause necrosis of the tumor cells by starvation. Facts show that, such treatment is applicable to perform vascular interventional treatment on almost all parenchymatous tumors.

Generally, in a relative large blood vessel (e.g., an operation on an arterial vessel at an initial stage), a guidewire is selected for the operation, and in a relative small vessel that is about to be entered upon proximity to the issues to be intervened, a micro guidewire with a smaller diameter is selected for the operation. Through guidance of the guidewire or the micro guidewire, a catheter or a micro catheter moves in the blood vessel along the guidewire or the micro guidewire until it reaches the tissue intended for intervention. However, since the catheter has certain flexibility, how to prevent the catheter from bending deformation, which affects the smooth process of an interventional treatment, is a problem worthy of study.

SUMMARY OF THE INVENTION

The objective of the present disclosure is to provide a catheter support apparatus and a transluminal intervention system, which have a simple structure, are easy to operate, and can well support a catheter to ensure the smooth completion of an interventional surgery.

In order to achieve the above objective, the present disclosure provides a catheter support apparatus. The catheter support apparatus includes a plurality of flexible supporting strips, and a plurality of meshing units arranged at intervals in a strip length direction are formed on each of the flexible supporting strips. The meshing units of the plurality of flexible supporting strips are at least partially meshed to jointly surround, define, and form a catheter placing cavity for accommodating a catheter.

In some embodiments, a flexible supporting strip has a chain shape and includes a plurality of chain segments, and adjacent chain segments are connected by passing a pin through them.

In some embodiments, a flexible supporting strip has a chain shape and includes a flexible belt and a plurality of chain segments, the plurality of chain segments are arranged at intervals on the flexible belt; or alternatively, the flexible supporting strip has an integrally-formed chain-like structure.

In some embodiments, a chain segment includes a chain segment plate and two meshing units arranged at intervals in a strip width direction of the flexible supporting strip, and the chain segment plate and the connected meshing units jointly surround and define an open accommodation groove. In two meshed flexible support strips, a plurality of open accommodation grooves are communicated to jointly form the catheter placing cavity.

In some embodiments, the number of the flexible support strips is two, and the meshing unit of each of the two flexible support strips includes: a meshing substrate, vertically arranged on the chain segment plate; and a meshing tooth, protruding from the meshing substrate in the strip length direction. The meshing tooth has a curved shape and extends in a surrounding manner to form a meshing protrusion and a meshing recess.

In some embodiments, a meshing unit of one of the two flexible support strips includes a meshing substrate vertically arranged on the chain segment plate and a meshing protrusion vertically protruding from the meshing substrate, and a meshing unit of the other of the two flexible support strips includes a meshing substrate vertically arranged on the chain segment plate and a meshing recess formed on the meshing substrate. The meshing recess and the meshing protrusion fit each other.

In some embodiments, the catheter support apparatus further includes a catheter zipper-chain guiderail for mounting the flexible support strips, and the catheter zipper-chain guiderail includes a main seat guiderail and two bifurcating seat guiderails formed by bifurcating at an end of the main seat guiderail.

In some embodiments, each of the flexible support strips includes an unmeshed flexible catheter zipper-chain bifurcating section and a meshed rigid catheter zipper-chain meshing section. The catheter zipper-chain meshing section is at least partially positioned within the main seat guiderail, and the catheter zipper-chain bifurcating section is at least partially positioned within a bifurcating seat guiderail.

In some embodiments, the bifurcating seat guiderails include a bifurcating front end connected to the main seat guiderail, and a guiding protrusion protruding towards the main seat guiderail is formed at the bifurcating front end, so that the meshing units of the two meshed zipper-chains are separated and enter respective bifurcating seat guiderails.

In some embodiments, a catheter insertion pore for inserting the catheter is further formed at the bifurcating front end, and the catheter insertion pore is arranged coaxially with an inner cavity of the main seat guiderail, so that the catheter is able to be inserted into the catheter placing cavity through the catheter insertion pore.

In some embodiments, the main seat guiderail is formed with a guiderail inner cavity, and the catheter placing cavity is positioned outside or inside the guiderail inner cavity.

In addition, the present disclosure further provides a transluminal intervention system, and the transluminal intervention system includes the above catheter support apparatus.

In some embodiments, the transluminal intervention system includes a system fixation seat and a sliding platform which is slidably mounted on the system fixation seat, and the catheter support apparatus is mounted on the sliding platform.

In some embodiments, the transluminal intervention system further includes a supporting strip braking assembly for locking the flexible supporting strips, and the supporting strip braking assembly includes:

an actuation wheel, wherein limiting grooves are formed on the chain segments, respectively, a plurality of actuation wheel limiting teeth that are distributed in circumference of the actuation wheel and are able to insert into the limiting grooves are formed on the actuation wheel; and a brake, which is mounted on the system fixation seat, wherein the actuation wheel is rotatably mounted onto the brake, and is switchable between a braking state and a free rotation state.

In the above technical solutions, the catheter support apparatus and the transluminal intervention system provided by the present disclosure adopt flexible supporting strips. By means of meshing units on the flexible supporting strips, the plurality of flexible supporting strips can be meshed and formed with a catheter placing cavity. By means of the catheter placing cavity, a catheter can be accommodated to enable wrapping of the catheter, thereby ensuring the support for the catheter. The catheter support apparatus has an effect of a certain anti-bending torque, and it has a simple structure and is easy to operate, thereby ensuring the smooth completion of an interventional surgery.

Other features and advantages of the present disclosure will be described in detail in the following section of Detailed Description of the Embodiments.

Figure 1:
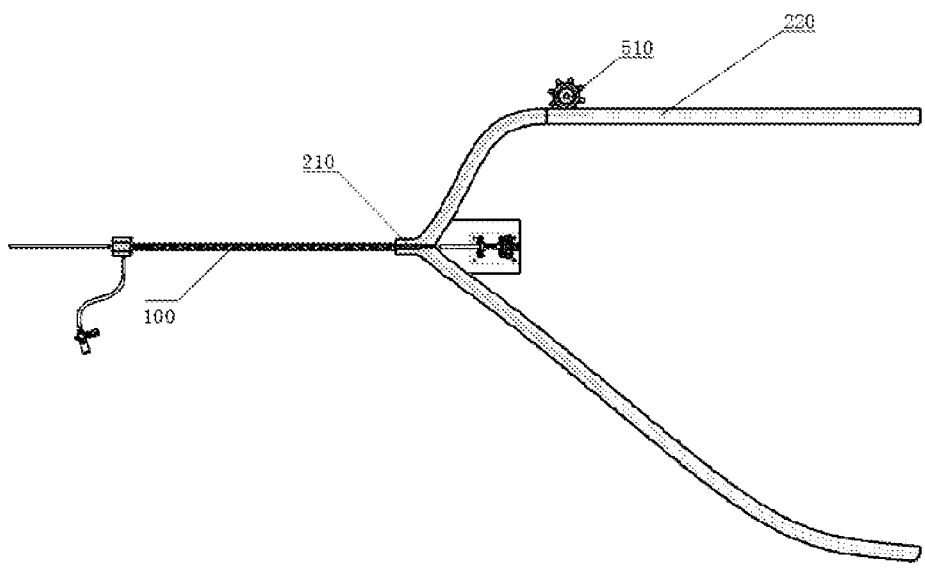
FIG. 1 schematically shows a structure of a catheter support apparatus provided by a specific embodiment of the present disclosure.

REFERENCE NUMERALS 100. chain segment; 200. catheter zipper-chain guiderail; 300. system fixation seat; 400. sliding platform; 500 supporting strip braking assembly; 110. chain segment plate; 120. meshing unit; 1210. meshing substrate; 1220. meshing protrusion; 1240. meshing recess; 210. main seat guiderail; 220. bifurcating seat guiderail; 510. actuation wheel; 520. brake; 1. catheter placing cavity; 2. pin; 3. open accommodation groove; 4. catheter zipper-chain meshing section; 5. catheter zipper-chain bifurcating section; 6. guiding protrusion; 7. catheter insertion pore; 8. limiting groove; 9. actuation wheel limiting tooth; 10. catheter; 11. flexible belt; 12. connection belt; L. strip length direction; W. strip width direction.

DETAILED DESCRIPTION OF THE EMBODIMENTS

Specific embodiments of the present disclosure are described in detail below with reference to accompanying drawings. It should be understood that, specific embodiments described herein are only used for illustrating and explaining the present disclosure and are not intended for limiting the present disclosure.

It should be noted that, embodiments in the present disclosure and features in the embodiments may combined with each other as long as no conflicts are resulted thereby.

The present disclosure will be described in detail with reference to the accompanying drawings in conjunction with the embodiments.

In intravascular interventional treatment, a catheter is guided to insert into a femoral artery of a patient via a guiding device, and is positioned near an opening of the artery. In general, a guidewire and the catheter are inserted into a blood vessel with a hemostasis valve, and then the guidewire is controlled to move in the vascular system until the guidewire reaches a lesion location. Generally, in a relative large blood vessel (i.e., an operation on an arterial vessel at an initial stage), a guidewire is selected for the operation, and in a relative small vessel that is about to be entered upon proximity to the issues to be intervened, a micro guidewire with a smaller diameter is selected for the operation. Through guidance of the guidewire or the micro guidewire, a catheter or a micro catheter moves in the blood vessel along the guidewire or the micro guidewire until it reaches the tissue intended for intervention. However, since the catheter has certain flexibility, how to prevent the catheter from bending deformation, which affects the smooth process of an interventional treatment, is a problem worthy of study.

For this reason, referring to FIG. 1 to FIG. 14, the present disclosure provides a catheter support apparatus, which includes a plurality of flexible supporting strips. A plurality of meshing units 120 arranged at intervals in a direction L of the length of the strip are formed on each flexible supporting strip. The meshing units 120 of the plurality of flexible supporting strips are at least partially meshed with one another to jointly surround, define, and form a catheter placing cavity 1 for accommodating a catheter 10. It can be understood that, the plurality of separate flexible supporting strips can mesh with each other to form a surrounding arrangement, so that the formed catheter placing cavity 1 can well wrap the catheter 10 to prevent the catheter 10 from bending during movement, thereby ensuring the smooth process of an interventional surgery.

Optionally, it should be noted that, the wording "flexible" may also be explained as flexibility, which is a property of an object relative to rigidity. Flexibility refers to a physical property that an object deforms under a force and cannot return to its original shape after the force is removed. The flexible supporting strips may be formed by a flexible material, such as rubber or plastic of certain flexibility. When the meshing units 120 of the flexible supporting strips have not meshed yet, the flexible supporting strips each can bend to a certain degree, and when it is required to perform meshing, meshing teeth and meshing recesses 1240 of the meshing units 120 complement each other and interlock to form meshing.

Optionally, the number of the flexible supporting strips may be two, three, four or more. For example, in the case of three flexible supporting strips, each of the flexible supporting strips is provided with two sets of meshing units 120 at an end in a direction W of the width of the strip, and three flexible supporting strips are arranged in parallel. At this time, one set of meshing units 120 of a first flexible supporting strip is able to mesh with one set of meshing units 120 of a second flexible supporting strip, the other set of meshing units 120 of the second flexible supporting strip is able to mesh with one set of meshing units 120 of a third flexible supporting strip, and the other set of meshing units 120 of the third flexible supporting strip is able to mesh with the other set of meshing units 120 of the first flexible supporting strip, so that a catheter placing cavity 1 is formed by surrounding in this manner.

Optionally, for a flexible supporting strip, it can be understood that, meshing units 120 thereof may cover a portion of the flexible supporting strip in the direction L of the length of the strip. In this way, regardless of the meshing units 120 being meshed totally or partially in the direction L of the length of the strip, a catheter support apparatus having a certain length of bifurcating section can be formed, thereby facilitating the adjustment of a length of a cavity tube of the catheter placing cavity 1 according to a length or position of the catheter 10.

Optionally, for the meshing units 120, in order to ensure the meshing units 120 on different flexible supporting strips can be meshed with each other, it is required that one of two meshed meshing units 120 is formed with a protruding tooth while the other one of the two meshed meshing units 120 is formed with a depressed recess. The tooth and the recess can fit each other in an arrangement manner similar to a zipper. Therefore, the meshing units 120 may have various shapes.

Figure 4:
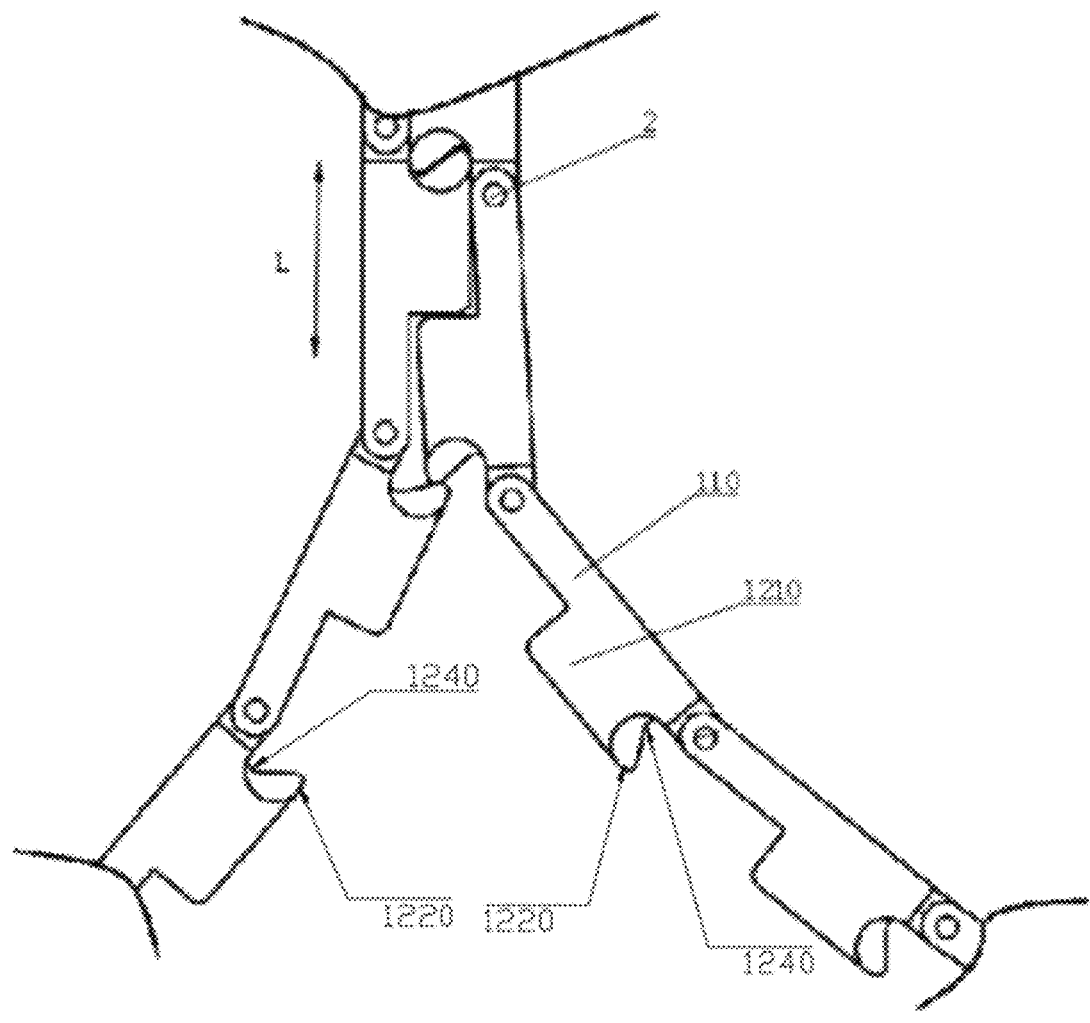
FIG. 4 schematically shows a structure from a perspective different from FIG. 3, in which chain segments are illustrated.

Specifically, the flexible supporting strip is a chain and comprises a plurality of chain segments 100, and adjacent chain segments 100 are connected with each other by passing a pin 2 through them. In an embodiment, as shown in FIG. 1, it can be understood that, a plurality of chain segments 100 are connected end-to-end by the pins 2 to form a flexible supporting chain. Correspondingly, the use of the pin 2 enables two adjacent chain segments 100 to have a certain rotational freedom degree therebetween. The flexible supporting strip may be understood as a catheter zipper-chain. When catheter zipper-chains have not meshed yet, adjacent chain segments 100 are connected sequentially by the pins. At this time, the chain segments 100 are in a completely unconstrained state in a spatial plane as shown in FIG. 4, and can be moved freely. That is, there are three freedom directions in a plane of a space (movement in two directions and rotation about an axis perpendicular to the plane). It can be understood that a catheter zipper-chain may be "flexible" at this time, and the chain-like morphology of the catheter zipper-chain may be freely changed. The existence of a catheter zipper-chain guiderail 200 provides a constraint on a proceeding movement direction when the catheter zipper-chains have not meshed yet.

Figure 12:
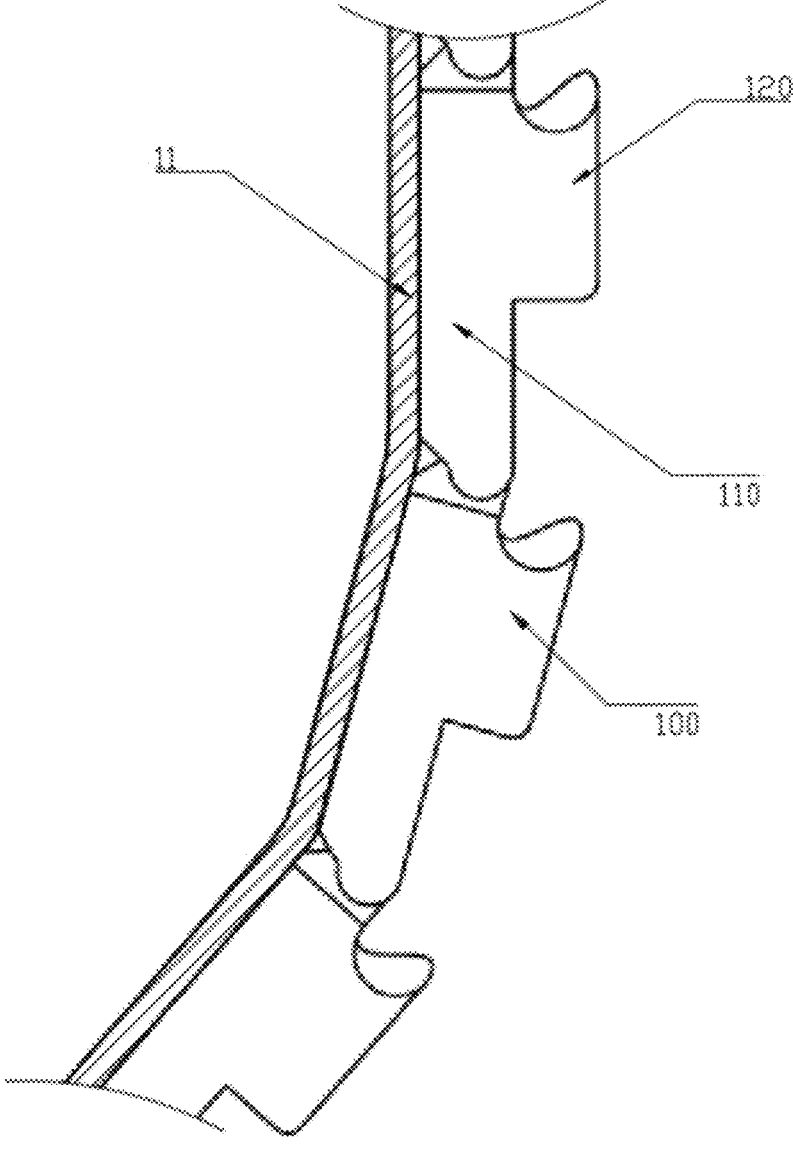
FIG. 12 schematically shows a structure of a flexible supporting strip provided by a specific embodiment of the present disclosure, in which a flexible belt and chain segments are illustrated.
Figure 14:
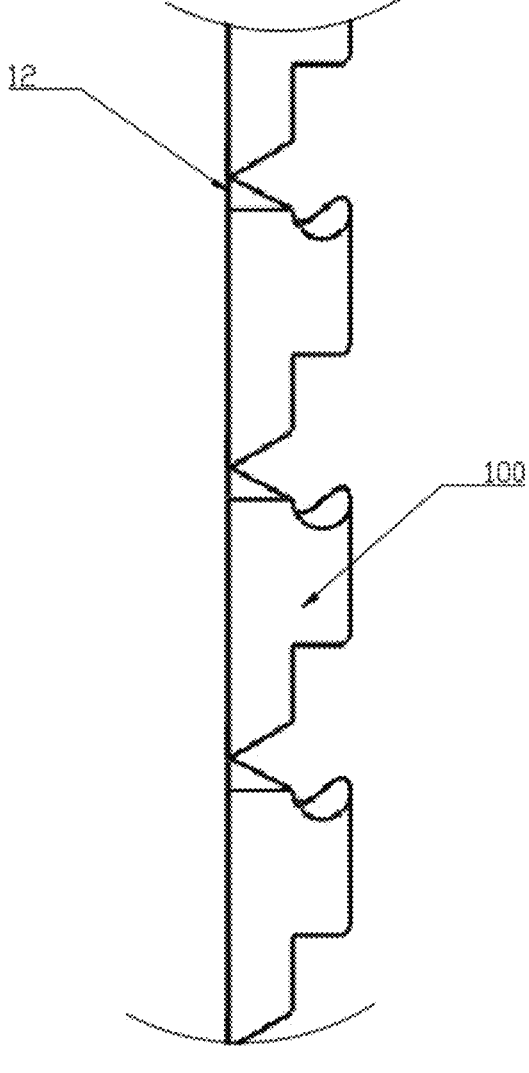
FIG. 14 schematically shows a structure of a flexible supporting strip provided by a specific embodiment of the present disclosure, in which a connection belt and chain segments which are integrally-formed are illustrated.

The flexible supporting strip has a chain shape, and includes a flexible belt 11 and a plurality of chain segments 100 which are arranged at intervals on the flexible belt 11; or alternatively, the flexible supporting strip has an integrally-formed chain-like structure. In an embodiment, as shown in FIG. 12, the flexible belt 11 has a flexible belt-like structure and has certain tenacity and strength, and the chain segments 100 may be attached and fixed on the flexible belt 11. The flexible belt 11 may be understood as a belt portion of a zipper, and the chain segments 100 may be understood as teeth of the zipper, so that a plurality of chain segments 100 have a certain movement freedom therebetween. That is, the catheter zipper-chains are "flexible", and the chain-like morphology may be freely changed. In another embodiment, as shown in FIG. 14, the flexible supporting strip has an integrally-formed chain-like structure, and includes a plurality of chain segments 100 and a connection belt 12 connected between two adjacent chain segments 100. By providing the connection belts 12 between adjacent chain segments 100, adjacent chain segments 100 can have a certain movement freedom therebetween, and the chain-like morphology can be freely changed.

When the chain segments of the catheter zipper-chains pass by a junction where the catheter zipper-chain at a main seat guiderail 210 joins with the catheter zipper-chains at bifurcating seat guiderails 220, due to a spatial constraint at the junction by a catheter zipper-chain guiderail 200, which mainly is a constraint after meshing in a direction of width, the chain segments 100 on opposite sides are sequentially meshed together according to concave and convex shapes that are matched. After meshing, the meshing restrains a left-right movement, a front-back movement, and a rotation of each meshing segment 100. This meshing is similar to fitting of an assembly, and it fully constrains the freedom of the meshed catheter zipper-chains in the spatial plane. Thus, the chain segments 100 cannot move freely, and the catheter zipper-chains can only translate as a whole. It can be understood that, the catheter zipper-chains are "rigid" at this time. The rigidity provides for the catheter 10 with spatial support, or in other words, an effect of an anti-bending torque. As mentioned above, the chain segments 100 are sequentially meshed together according to the matched concave and convex shapes, just like the zipper of a piece of clothing, so it is called a catheter zipper-chain. It should be noted that, the so-called "rigidity" after the meshing of the catheter zipper-chains is a relative extent. With the increasing of a meshing or matching tolerance, the catheter zipper-chains after the meshing have flexibility to some extent, but practice has proven that the flexibility does not affects its functional use.

In this way, the flexible support strips formed by a plurality of chain segments 100 have certain rigidity after the meshing, and can provide a better stable support to the catheter 1. In addition, it should be noted that, the pin 2 may be an integrally-formed structure extending from a chain segment 100 or an independent structure, for which specific limitations are not made any further herein.

Figure 3:
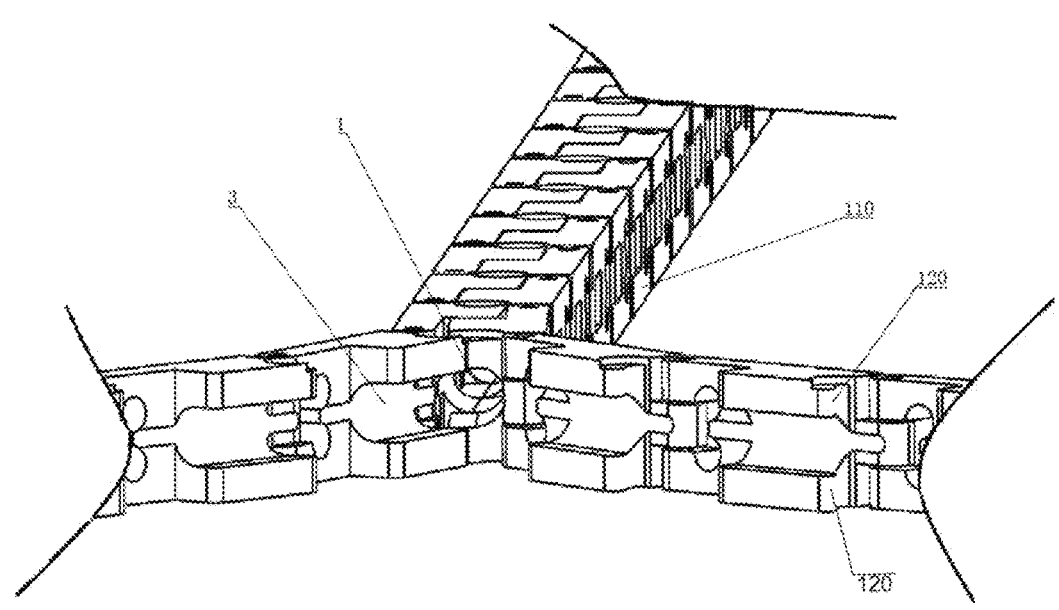
FIG. 3 schematically shows a structure of flexible supporting strips provided by a specific embodiment of the present disclosure.
Figure 5:
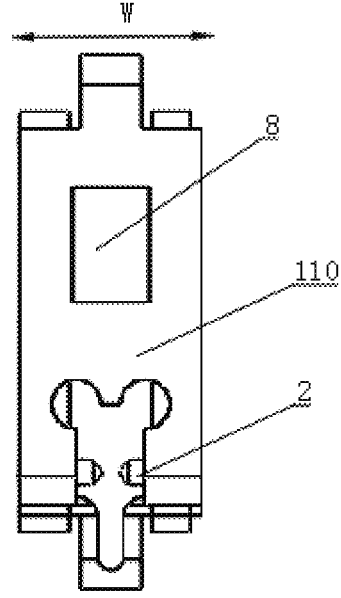
FIG. 5 schematically shows a partial structure from a perspective different from FIG. 4, in which a set of meshed chain segments is illustrated.

Further, for a specific structure of the chain segment 100, in an embodiment, the chain segment 100 includes a chain segment plate 110 and two meshing units 120 arranged at intervals in the direction W of the width of the flexible support strip, and the chain segment plate 110 and the meshing units 120 connected to the plate jointly surround and define an open accommodation groove 3. In a case where two flexible support strips mesh, a plurality of open accommodation grooves 3 are in communication to jointly form the catheter placing cavity 1. As shown in FIG. 3 and FIG. 5, it can be understood that, the chain segment 100 has a three-sided frame ("□") shape, and the chain segment plate 110 and the meshing units 120 may be an integrally-formed structure. In this way, it is easy to process, and the structure has better stability. Further, the chain segment plate 110 and the meshing units 120 may form the open accommodation groove 3 in a surrounding manner, and at this time the catheter can be placed in the open accommodation groove 3 without obstacles. Further, two chain segments 100 having the three-sided frame shape are meshed with each other by the meshing units 120, and the open accommodation grooves 3 can form a closed catheter placing cavity 1. In this way, wrapping of the catheter 10 can be implemented, and supporting of the catheter 10 can be ensured, thereby achieving an effect of a certain anti-bending torque.

Furthermore, in an embodiment, the number of the flexible support strips is two, and each of the two flexible support strips includes: a meshing substrate 1210, vertically arranged on the chain segment plate 110; and a meshing tooth, protruding from the meshing substrate 1210 in the direction L of the length of the strip. The meshing tooth has a curved shape, and extends in a surrounding manner to form a meshing protrusion 1220 and a meshing recess 1240. As shown in FIG. 3 and FIG. 4, it can be understood that, the chain segments 100 of the two flexible support strips have the same structure. At this time, by means of the meshing substrate 1210, the chain segment 100 is formed with the open accommodation groove 3 that is sufficient to accommodate the catheter 10, and by means of the meshing teeth, meshing of the two meshing units 120 is enabled. Specifically, two chain segments 100 to be meshed are arranged oppositely in the direction L of the length of the strip. In this way, the meshing tooth of one of the two meshed chain segments 100 can be exactly meshed with the meshing tooth of the other one of the two meshed chain segments 100. That is, a meshing protrusion 1220 of one of the two flexible support strips can insert into a meshing recesses 1240 of the other of the two flexible support strips, so as to form a circular structure through split joint, specifically the chain segment 100 as shown in FIG. 4. The product has a simple structure and is easy to process.

Figure 6:
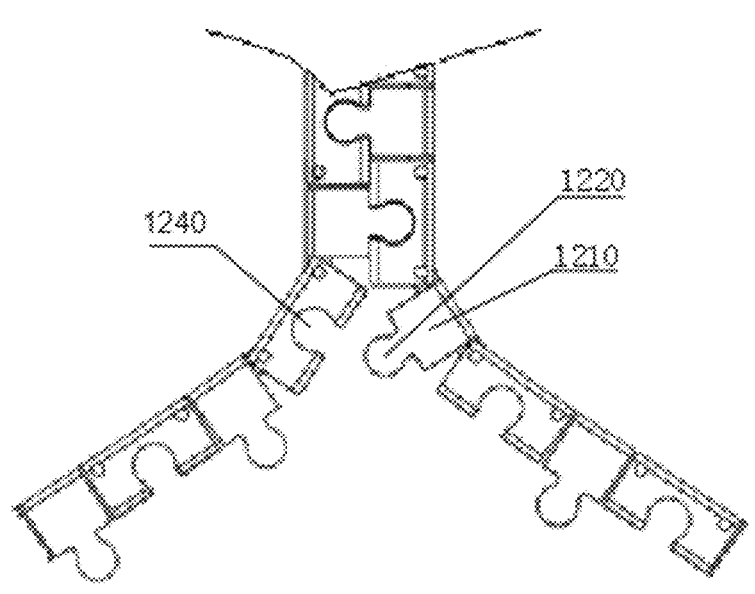
FIG. 6 schematically shows a structure of the flexible supporting strips provided by a specific embodiment of the present disclosure.

Furthermore, in another embodiment, a meshing unit 120 of one of the two flexible support strips includes a meshing substrate 1210 vertically arranged on a chain segment plate 110 and a meshing protrusion 1220 vertically protruding from the meshing substrate 1210, and a meshing unit 120 of the other of the two flexible support strips includes a meshing substrate 1210 vertically arranged on a chain segment plate 110 and a meshing recess 1240 formed in the meshing substrate 1210. The meshing recess 1240 and the meshing protrusion 1220 fit each other. As shown in FIG. 6, with respect to various flexible support strips, two meshed chain segments 100 thereof that are to be meshed may have different structures. For example, the two meshed chain segments 100 may both have meshing substrates 1210, and correspondingly, one meshing substrate 1210 is formed with a notch serving as the meshing recess 1240, and the other meshing substrate 1210 is formed with a protruding meshing protrusion 1220 in a direction of the height of the meshing substrate 1210. In this way, the meshing protrusion 1220 can be meshed with the meshing recess 1240, thereby realizing quick meshing of the two chain segments 100.

Figure 2:
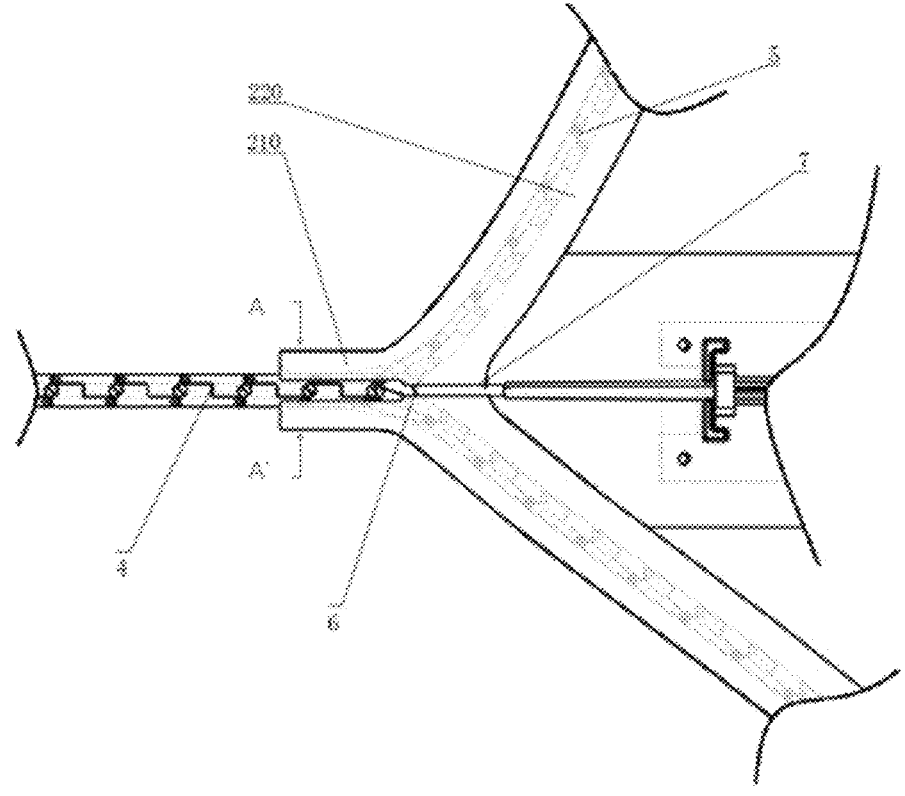
FIG. 2 schematically shows a partial structure of FIG. 1, in which a catheter zipper-chain meshing section and catheter zipper-chain bifurcating sections are illustrated.
Figure 10:
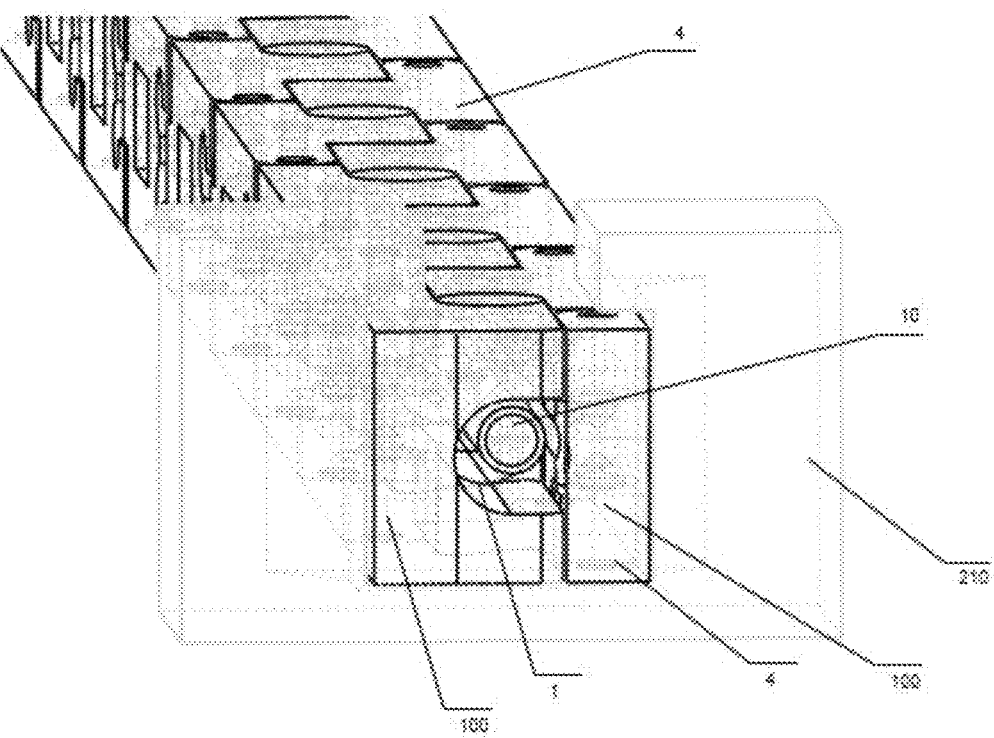
FIG. 10 schematically shows a structure of an cross section along A-A' from a perspective different from FIG. 2.

In addition, in order to facilitate the adjustment of a length of the catheter placing cavity 1 according to a length and an orientation of a catheter, in an embodiment, the catheter support apparatus further includes a catheter zipper-chain guiderail 200 for assembling the flexible support strips. The catheter zipper-chain guiderail 200 includes a main seat guiderail 210 and two bifurcating seat guiderails 220 formed by bifurcating at an end of the main seat guiderail 210. Further, a flexible support strip includes an unmeshed flexible catheter zipper-chain bifurcating section 5 and a meshed rigid catheter zipper-chain meshing section 4. The catheter zipper-chain meshing section 4 is at least partially positioned within the main seat guiderail 210, and the catheter zipper-chain bifurcating section 5 is at least partially positioned within the bifurcating seat guiderail 220. As shown in FIG. 1 and FIG. 2, it can be understood that, a junction or a bifurcating portion of the catheter zipper-chain guiderail 200 is similar to a slider of a zipper structure, and can help to guide two flexible support strips to mesh with or separate from each other. As shown in FIG. 10, specifically, the catheter zipper-chain guiderail 200 is able to restrict a movement path of the flexible support strips. The main seat guiderail 210 is able to accommodate the catheter zipper-chain meshing section 4, and the bifurcating seat guiderails 220 are able to accommodate two catheter zipper-chain bifurcating sections 5. For example, when the meshing protrusions 1220 and the meshing recesses 1240 are meshed sequentially, complementing and interlocking of the meshing restrict the individual movement freedom of each chain segment 100, so that the catheter zipper-chain meshing section 4 formed after the meshing is rigid.

In addition, a portion of each of the flexible support strips is always accommodated, in the form of the catheter zipper-chain bifurcating section 5, within the bifurcating seat guiderail 220, and a portion of each of the flexible support strips is always accommodated, in the form of the catheter zipper-chain meshing section 4, within the main seat guiderail 210. When it is needed to increase a length of the catheter zipper-chain meshing section 4, it is simply required to pull the catheter zipper-chain meshing section 4 to allow the catheter zipper-chain bifurcating sections 5 to enter the main seat guiderail 210. When it is needed to shorten the length of the catheter zipper-chain meshing section 4, it is simply required to push the catheter zipper-chain guiderail 200 towards the catheter zipper-chain meshing section 4 to allow the catheter zipper-chain meshing section 4 to turn into the catheter zipper-chain bifurcating sections 5 so as to implement separation.

Further, in an embodiment, the bifurcating seat guiderails 220 together include a bifurcating front end connected to the main seat guiderail 210, and a guiding protrusion 6 protruding towards the main seat guiderail 210 is formed at the bifurcating front end, by means of which the meshed meshing units 120 of two zipper-chains are separated and enter respective bifurcating seat guiderails 220. As shown in FIG. 2, it can be understood that, the guiding protrusion 6 may be formed at a joint where the bifurcating seat guiderails 220 link to the main seat guiderail 210, and the guiding protrusion 6 may be a triangular structure with a tip facing the main seat guiderail 210. When the catheter zipper-chain meshing section 4 passes by the guiding protrusion 6, under the combined action of the guiding protrusion 6 and the catheter zipper-chain bifurcating sections 5, two meshed meshing units 120 are separated from each other. In this way, by the movement of the catheter zipper-chain guiderail 200, the length of the catheter zipper-chain meshing section 4 can be adjusted quickly and conveniently, so as to adapt to the movement of the catheter 10.

Further, in an embodiment, a catheter insertion pore 7 for inserting the catheter 10 is further formed at the bifurcating front end, and the catheter insertion pore 7 is arranged coaxially with an inner cavity of the main seat guiderail 210. As shown in FIG. 2, the catheter 10 can be inserted into the main seat guiderail 210 through the catheter insertion pore 7, and meanwhile the catheter insertion pore 7 is arranged coaxially with the main seat guiderail 210, so that the catheter 10 can be inserted into the catheter placing cavity 1 through the catheter insertion pore 7. In this way, the catheter 10 can be inserted into the catheter zipper-chain meshing section 4 conveniently and precisely. The structure is simple, and is easy for operating with high precision.

Figure 13:
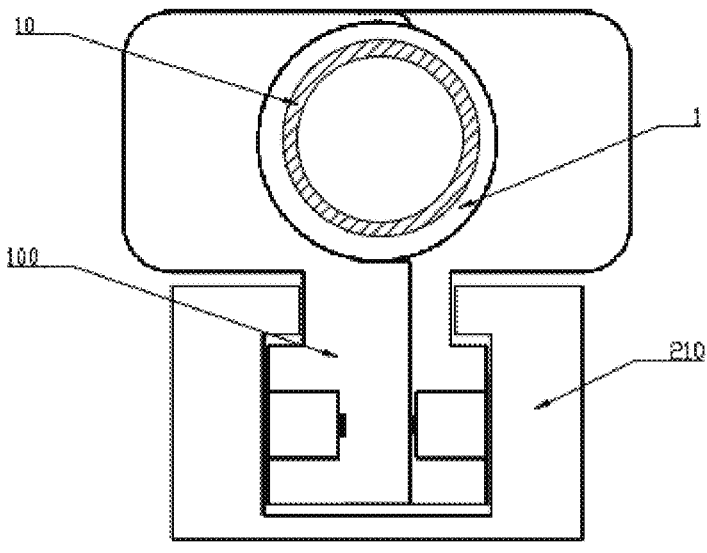
FIG. 13 schematically shows a structure, in which a catheter placing cavity is positioned outside a main seat guiderail, provided by a specific embodiment of the present disclosure.

For the positional relationship between the catheter placing cavity 1 and the main seat guiderail 210, in an embodiment, the main seat guiderail 210 is formed with a guiderail inner cavity, and the catheter placing cavity 1 is positioned outside or inside the guiderail inner cavity. As shown in FIG. 13, it can be understood that, the chain segment 100 includes a first portion positioned inside the guiderail inner cavity and a second portion positioned outside the guiderail inner cavity. In this way, the chain segment 100 is fixed on the main seat guiderail 210 by the first portion, and the catheter 10 is accommodated and wrapped by the second portion. Alternatively, in another embodiment, the main seat guiderail 210 is formed with a guiderail inner cavity, and the catheter placing cavity 1 is positioned inside the guiderail inner cavity. As shown in FIG. 10, the chain segment 100 is fully wrapped inside the main seat guiderail 210. In this way, the chain segment 100 and the catheter 10 can be better protected.

In addition, the present disclosure further provides a transluminal intervention system, which includes the above catheter support apparatus.

Figure 7:
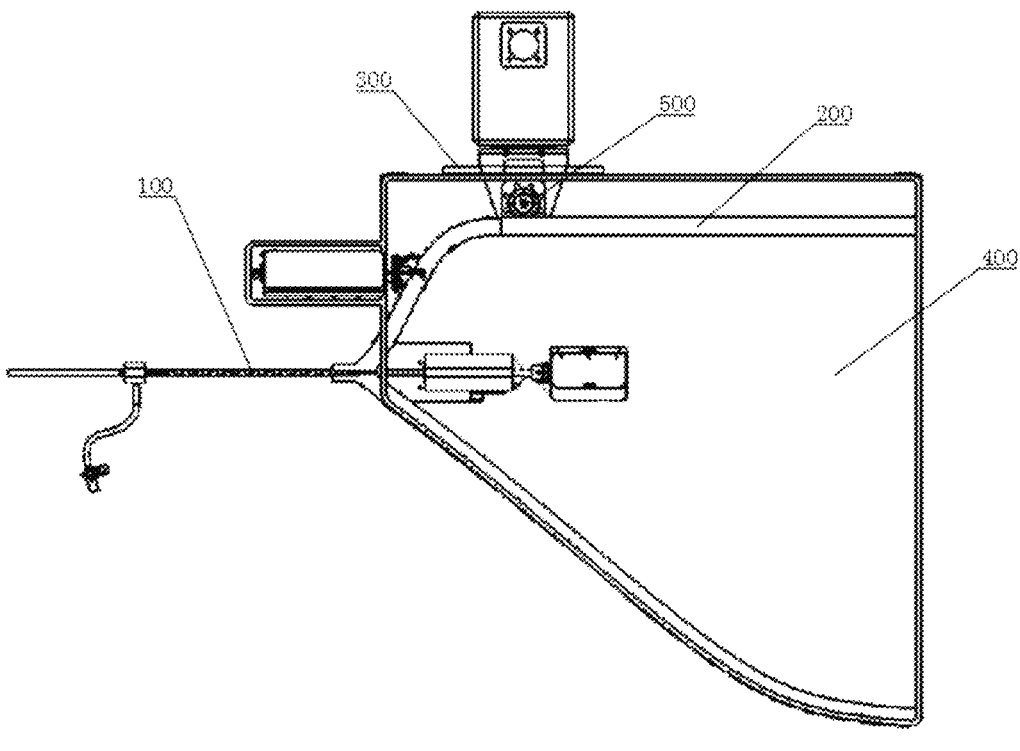
FIG. 7 schematically shows a structure of a transluminal intervention system provided by a specific embodiment of the present disclosure.
Figure 8:
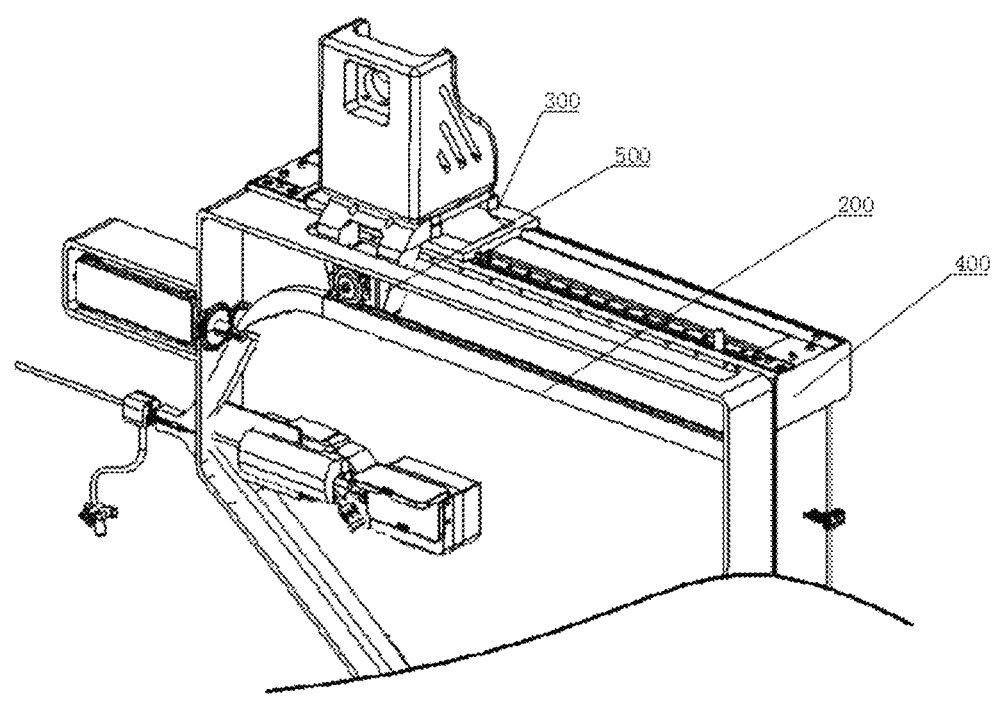
FIG. 8 schematically shows a three-dimensional structure from a perspective different from FIG. 7.

In an embodiment, the transluminal intervention system comprises a system fixation seat 300 and a sliding platform 400 which is slidably mounted on the system fixation seat 300, and the catheter support apparatus is mounted on the sliding platform 400. As shown in FIG. 7 and FIG. 8, the system fixation seat 300 may be a fixed end of the system, and the sliding platform 400 may be a movable end of the system and is configured for assembling a structure required in an interventional treatment surgery, such as a catheter guidewire.

In the interventional surgery, first, a catheter sheath is inserted into a puncture point of the body tissue. A distal end (front end) of the catheter 10 is inserted into the catheter sheath, and then a proximal end (rear end) of the catheter 10 is mounted on the sliding platform 400 at a location where the catheter zipper-chains bifurcate from each other so as to be inserted into the catheter insertion pore 7. Then, the catheter zipper-chains are pulled out, and the catheter zipper-chains are gradually meshed, extend, and meanwhile wrap the catheter 10 until sheath clamps at leading ends of the catheter zipper-chains are dragged to the catheter sheath. The catheter sheath is mounted in the sheath clamps, and when the sheath clamps are dragged, the sheath clamps can exert a pulling force on the catheter zipper-chain meshing section 4. In this way, portions of the catheter zipper-chain bifurcating sections 5 are meshed to form the catheter zipper-chain meshing section 4, so as to increase the length of the catheter zipper-chain meshing section 4, and meanwhile the whole formed catheter placing cavity 1 wraps the catheter 10. Since the catheter zipper-chain bifurcating sections 5 that are meshed together have certain rigidity, the catheter 10 can be supported thereby.

Figure 9:
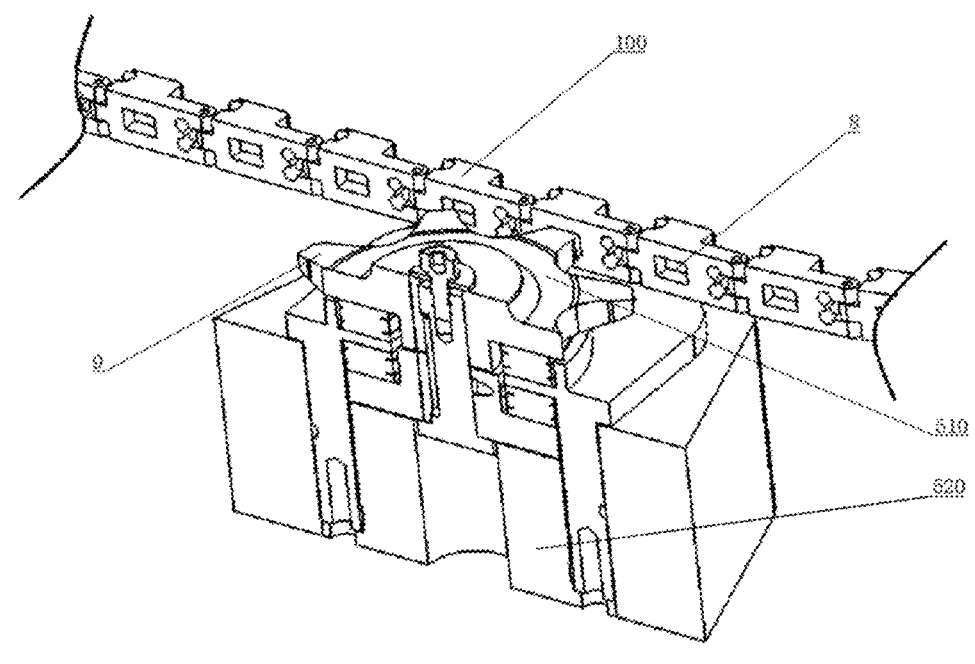
FIG. 9 schematically shows a partial three-dimensional structure from a perspective different from FIG. 8, in which chain segments and an actuation wheel are illustrated.

Further, for braking of the flexible supporting strips, in an embodiment, the transluminal intervention system further includes a supporting strip braking assembly 500 for fixing the flexible supporting strips. The supporting strip braking assembly 500 includes: an actuation wheel 510, wherein limiting grooves 8 are formed on chain segments 100, respectively, and a plurality of actuation wheel limiting teeth 9 that are distributed in a circumference of the actuation wheel and are able to insert into the limiting grooves 8 are formed on the actuation wheel 510; and a brake 520, which is mounted on the system fixation seat 300. The actuation wheel 510 is rotatably mounted onto the brake 520, and is switchable between a braking state and a free rotation state. As shown in FIG. 8 and FIG. 9, the brake 520 is mounted on the system fixation seat 300, and the actuation wheel 510 inserts into the catheter zipper-chain guiderail 200. The actuation wheel 510 extends in and goes through the sliding platform 400 and a sliding notch is formed therefor, so that when positional shifting happens between the system fixation seat 300 and the sliding platform 400, the actuation wheel 510 and the sliding platform 400 do not interfere with each other.

Specifically, the brake 520 can control a movement state of the actuation wheel 510 by being powered on or powered off. When the brake 520 is in a powered-off state, the actuation wheel 510 is in a free rotation state and can rotate freely. The limiting groove 8 formed on the chain segment 100 and the actuation wheel limiting tooth 9 on the actuation wheel 510 fit each other. Along with the positional shifting of the flexible support strips, the actuation wheel 510 can rotate and allow a portion of an actuation wheel limiting tooth 9 to insert into a limiting groove 8. When it is needed to lock the flexible support strips, the brake 520 may be powered on. At this time, the actuation wheel 510 is in a braking state and cannot continue to rotate, and due to the fit relationship between the actuation wheel limiting teeth 9 and the limiting grooves 8, the position of the flexible support strips is locked. In addition, other specific structures of the supporting strip braking assembly 500 are existing technologies in the art, and details thereof are not described any further.

Correspondingly, in order to ensure the interaction between the actuation wheel 510 and the limiting grooves 8 of the chain segments 100, it is needed to arrange an opening in the bifurcating seat guiderail 220 at a side facing the actuation wheel 510, so that the actuation wheel 510 is connected to the corresponding chain segments 100 without obstacles.

First, a direction of the distal end (the front end) is defined as a forward direction while the flexible support strips are being dragged forward, and a direction of the proximal end (the rear end) is defined as a backward direction while the flexible support strips are being dragged backward. An interventional surgery using the transluminal intervention system may be implemented as follows: when the brake 520 in the powered-off state, the actuation wheel 510 is in the free rotation state at this time, a sheath tube of the catheter sheath is inserted into a reserved punctured site of a patient, and the proximal end (the rear end) of the catheter 10 is mounted on the sliding platform 400 at a location where the catheter zipper-chains bifurcate from each other so as to be inserted into the catheter insertion pore 7; then, the catheter zipper-chains are pulled out, so that catheter zipper-chains are meshed and elongated along with wrapping the catheter 10 until the sheath clamps at the leading ends of the catheter zipper-chains is dragged to the catheter sheath, and at this time the flexible support strips form the catheter placing cavity 1 having a certain length.

In subsequent operations, a superselective catheterization interventional treatment of the kidney is taken as an example. First, the catheter 10 needs to reach a predetermined reasonable position. In general, a guidewire goes through the catheter 10 and extends beyond the catheter 10 by a small distance, and a specific curved shape at a tip of the guidewire is used to select a vascular branch of the femoral artery. After selecting a correct vascular branch by using the guidewire, the guidewire stays still, and then the catheter 10 mounted on the sliding platform 400 goes forward "along" the guidewire through feeding movement of the sliding platform 400 towards the distal end (the front end). After that, the guidewire is fed again to allow the tip of the guidewire to extend beyond the catheter 10 by a certain distance, and the catheter is fed along the guidewire again. In this way, the catheter 10 and the guidewire go forward alternately. In a relative large femoral artery vessel or at an artery branch that is easy to enter, the catheter 10 and the guidewire may be fed together and go forward directly so as to continue operations of the interventional surgery.

Figure 11:
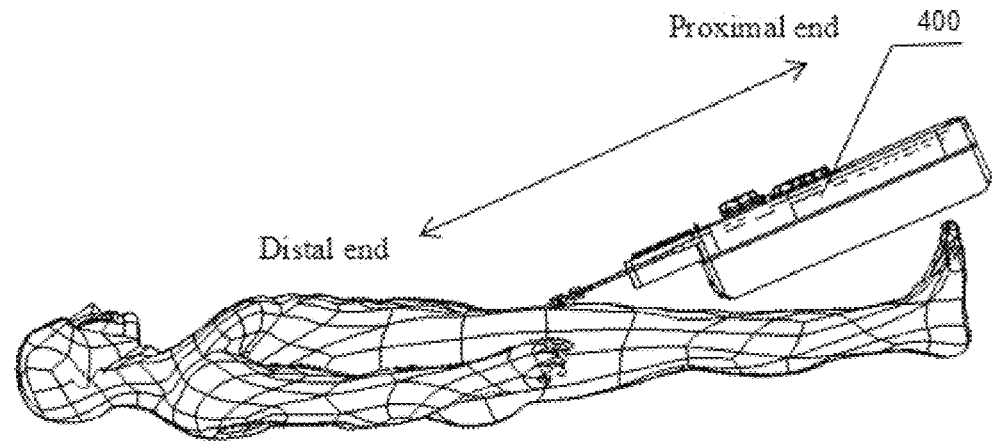
FIG. 11 schematically shows a structure of the transluminal intervention system provided by a specific embodiment of the present disclosure.

As shown in FIG. 11, when the catheter 10 is fed forward with movement of the sliding platform 400, it is required that the actuation wheel 510 should be in the braking state. That is, the flexible support strips and a mechanical arm are in a stationary locking state. However, the catheter zipper-chain guiderail 200 is fed together with the sliding platform 400. At this time, the flexible support strips seems to slide in the catheter zipper-chain guiderail 200 relative to the catheter zipper-chain guiderail 200, but the flexible support strips are stationary while the catheter zipper-chain guiderail 200 is in motion. As the sliding platform 400 and the catheter zipper-chain guiderail 200 are fed forward together, the length of the catheter zipper-chain meshing section 4 by which the flexible support strips extend beyond the catheter zipper-chain guiderail 200 is shortened. Likewise, inversely, when the flexible support strips are stationary, as the sliding platform 400 and the catheter zipper-chain guiderail 200 go backward, the length of the catheter zipper-chain meshing section 4 by which the flexible support strips extend beyond the catheter zipper-chain guiderail 200, i.e., the length of the meshed meshing units by which the catheter zipper-chain extends beyond the guiderail, is lengthened. A portion of the catheter between an operating end and the catheter sheath is lengthened or shortened depends on the interventional surgery operations, and the flexible support strips may also be lengthened or shortened along with this portion of the catheter.

It should be noted in particular that, the catheter support apparatus and other configurations and functions of the transluminal intervention system according to embodiments of the present disclosure are known to those of ordinary skills in the art, for example a structure for actuating the guidewire and the catheter to move or rotate. For the sake of brevity, details are not described herein.

Preferred embodiments of the present disclosure are described with reference to the accompanying drawings, but the present disclosure is not limited to specific details of the above implementation manners, and simple variations can be made to technical solutions of the present disclosure within the scope of the technical concept of the present disclosure.

In addition, wordings such as "first" and "second" are only used for the purpose of description only, and should not be understood as indicating or suggesting relative importance or implicitly indicating the number of technical features referred to. Accordingly, a feature defined by "first" and "second" may indicate or suggest that at least one said feature is included. In the description of the present disclosure, "a plurality of" means at least two, for example, two, three, and the like, unless expressively defined otherwise.

In the present disclosure, unless expressively specified and defined otherwise, terms such as "mount/assemble", "connect to", "connect", and "fix/lock" should be interpreted broadly. For example, it may be a fixed connection, a detachable connection, or an integral connection; it may be a mechanical connection or an electrical connection or a communicative connection; and it may be a direct connection, an indirect connection by means of an intermediary, or an internal communication between two elements or an interactive relationship between two elements, unless expressively defined otherwise. For those of ordinary skills in the art, specific meanings of the above terms in the present disclosure may be understood according to specific situations.

In the present disclosure, unless expressively specified and defined otherwise, a first feature being at an "upper" or "lower" position than a second feature may mean that the first feature and the second feature are in a direct contact or in an indirect contact via an intermediary. Moreover, a first feature being "above", "over", or "on top of" the second feature may mean that the first feature is directly above, diagonally above, or simply at a higher horizontal level than the second feature. The first feature being "below", "under", or "beneath" the second feature may mean that the first feature is directly below, diagonally below, or simply at a lower horizontal level than the second feature.

In the description of this specification, descriptions with reference to wordings such as "one embodiment", "some embodiments", "example", "specific example", or "some examples" indicate that specific features, structures, materials, or characteristics described in conjunction with the embodiments or examples are included within at least one embodiment or example of the present disclosure. In the present specification, the illustrative expressions of the above terms do not necessarily refer to the same embodiment or example. Moreover, the specific features, structures, materials, or characteristics described may be combined in any suitable manner in any one or more embodiments or examples. Furthermore, different embodiments or examples and features in different embodiments or examples can be integrated and combined by those skilled in the art without any mutual contradiction.

Although embodiments of the present disclosure have been shown and described above, it can be understood that the above embodiments are illustrative and should not be construed as limiting the present disclosure. Structural changes, modifications, substitutions, and variations made on the features of the present disclosure are all within the protection scope of the present disclosure.

What is claimed is:

1. A catheter support apparatus comprising:

a plurality of flexible supporting strips comprising a plurality of meshing units, wherein:

each flexible supporting strip, of the plurality of flexible supporting strips, comprises two or more meshing units, of the plurality of meshing units, arranged at intervals in a strip length direction (L) of the flexible supporting strip;

each meshing unit of a flexible supporting strip is configured to be at least partially meshed to a meshing unit of the two or more meshing units of a different flexible supporting strip of the plurality of flexible supporting strips, such that the plurality of meshing units, when meshed together, jointly surround, define, and form a catheter placing cavity for accommodating a catheter; and each of the flexible supporting strips has a chain shape and comprises a plurality of chain segments.

2. The catheter support apparatus according to claim 1, wherein adjacent chain segments are connected with each other by passing a pin through them.

3. The catheter support apparatus according to claim 1, wherein:

each of the flexible supporting strips further comprises a flexible belt, and the plurality of chain segments are arranged at intervals on the flexible belt; or each of the flexible supporting strips has an integrally-formed chain-like structure.

4. The catheter support apparatus according to claim 2, wherein each of the plurality of chain segments comprises a chain segment plate and two meshing units arranged at intervals in a strip width direction (W) of the flexible supporting strip, the chain segment plate and the meshing units connected to the plate jointly surround and define an open accommodation groove, and in two flexible support strips that are meshed with each other, a plurality of open accommodation grooves are communicated to jointly form the catheter placing cavity.

5. The catheter support apparatus according to claim 4, wherein a quantity of the flexible support strips is two, and a meshing unit of each of the two flexible support strips comprises:

a meshing substrate, vertically arranged on the chain segment plate; and a meshing tooth, protruding from the meshing substrate in the strip length direction (L), wherein the meshing tooth has a curved shape and extends in a surrounding manner to form a meshing protrusion or a meshing recess.

6. The catheter support apparatus according to claim 4, wherein a meshing unit of one of the two flexible support strips comprises a meshing substrate vertically arranged on the chain segment plate and a meshing protrusion vertically protruding from the meshing substrate, a meshing unit of the other of the two flexible support strips comprises a meshing substrate vertically arranged on the chain segment plate and a meshing recess formed on the meshing substrate, and the meshing recess and the meshing protrusion fit each other.

7. The catheter support apparatus according to claim 2, wherein the catheter support apparatus further comprises a catheter zipper-chain guiderail for mounting the flexible support strips, and the catheter zipper-chain guiderail comprises a main seat guiderail and two bifurcating seat guiderails formed by bifurcating at an end of the main seat guiderail.

8. The catheter support apparatus according to claim 7, wherein the flexible support strip comprises an unmeshed flexible catheter zipper-chain bifurcating section and a meshed rigid catheter zipper-chain meshing section, wherein the catheter zipper-chain meshing section is at least partially positioned within the main seat guiderail, and the catheter zipper-chain bifurcating section is at least partially positioned within a bifurcating seat guiderail of the two bifurcating seat guiderails.

9. The catheter support apparatus according to claim 8, wherein the bifurcating seat guiderails comprise a bifurcating front end connected to the main seat guiderail, and a guiding protrusion protruding towards the main seat guiderail is formed at the bifurcating front end, so that the meshing units of two meshed zipper-chains are separated and enter respective bifurcating seat guiderails.

10. The catheter support apparatus according to claim 9, wherein a catheter insertion pore for inserting the catheter is further formed at the bifurcating front end, and the catheter insertion pore is arranged coaxially with an inner cavity of the main seat guiderail, so that the catheter is able to be inserted into the catheter placing cavity through the catheter insertion pore.

11. The catheter support apparatus according to claim 8, wherein the main seat guiderail is formed with a guiderail inner cavity, and the catheter placing cavity is positioned outside or inside the guiderail inner cavity.

12. A transluminal intervention system comprising:

a catheter support apparatus;

a system fixation seat; and a sliding platform which is slidably mounted on the system fixation seat, wherein the catheter support apparatus is mounted on the sliding platform, wherein the catheter support apparatus comprises a plurality of flexible supporting strips, the plurality of flexible supporting strips comprising a plurality of meshing units, and wherein:

each flexible supporting strip, of the plurality of flexible supporting strips, comprises two or more meshing units, of the plurality of meshing units, arranged at intervals in a strip length direction (L) of the flexible supporting strip;

each meshing unit of a flexible supporting strip is configured to be at least partially meshed to a meshing unit of the two or more meshing units of a different flexible supporting strip of the plurality of flexible supporting strips, such that the plurality of meshing units, when meshed together, jointly surround, define, and form a catheter placing cavity for accommodating a catheter;

each of the flexible supporting strips has a chain shape and comprises a plurality of chain segments; and adjacent chain segments are connected with each other by passing a pin through them.

13. The transluminal intervention system according to claim 12, further comprising a supporting strip braking assembly for locking the flexible supporting strips, wherein the supporting strip braking assembly comprises:

an actuation wheel, wherein limiting grooves are formed on the chain segments, respectively, a plurality of actuation wheel limiting teeth that are distributed in a circumference of the actuation wheel and are able to insert into the limiting groove are formed on the actuation wheel; and a brake, which is mounted on the system fixation seat;

wherein the actuation wheel is rotatably mounted onto the brake, and is switchable between a braking state and a free rotation state.

14. The transluminal intervention system according to claim 12, wherein:

each of the flexible supporting strips further comprises a flexible belt, and the plurality of chain segments are arranged at intervals on the flexible belt; or each of the flexible supporting strip has an integrally-formed chain-like structure.

15. The transluminal intervention system according to claim 12, wherein each of the plurality of chain segments comprises a chain segment plate and two meshing units arranged at intervals in a strip width direction (W) of the flexible supporting strip, the chain segment plate and the meshing units connected to the plate jointly surround and define an open accommodation groove, and in two flexible support strips that are meshed with each other, a plurality of open accommodation grooves are communicated to jointly form the catheter placing cavity.

16. The transluminal intervention system according to claim 15, wherein a quantity of the flexible support strips is two, and a meshing unit of each of the two flexible support strips comprises:

a meshing substrate, vertically arranged on the chain segment plate; and a meshing tooth, protruding from the meshing substrate in the strip length direction (L), wherein the meshing tooth has a curved shape and extends in a surrounding manner to form a meshing protrusion or a meshing recess.

17. The transluminal intervention system according to claim 15, wherein a meshing unit of one of the two flexible support strips comprises a meshing substrate vertically arranged on the chain segment plate and a meshing protrusion vertically protruding from the meshing substrate, a meshing unit of the other of the two flexible support strips comprises a meshing substrate vertically arranged on the chain segment plate and a meshing recess formed on the meshing substrate, and the meshing recess and the meshing protrusion fit each other.

18. The transluminal intervention system according to claim 12, wherein the catheter support apparatus further comprises a catheter zipper-chain guiderail for mounting the flexible support strips, and the catheter zipper-chain guiderail comprises a main seat guiderail and two bifurcating seat guiderails formed by bifurcating at an end of the main seat guiderail.

19. The transluminal intervention system according to claim 18, wherein the flexible support strip comprises an unmeshed flexible catheter zipper-chain bifurcating section and a meshed rigid catheter zipper-chain meshing section, wherein the catheter zipper-chain meshing section is at least partially positioned within the main seat guiderail, and the catheter zipper-chain bifurcating section is at least partially positioned within a bifurcating seat guiderail of the two bifurcating seat guiderails.

20. The transluminal intervention system according to claim 19, wherein the bifurcating seat guiderails comprise a bifurcating front end connected to the main seat guiderail, and a guiding protrusion protruding towards the main seat guiderail is formed at the bifurcating front end, so that the meshing units of two meshed zipper-chains are separated and enter respective bifurcating seat guiderails.

* * * * *